United States Patent [19]

DeLuca et al.

[11] Patent Number: 5,721,225
[45] Date of Patent: Feb. 24, 1998

[54] 18, 19-DINOR-VITAMIN D COMPOUNDS

[75] Inventors: Hector F. DeLuca, Deerfield, Wis.; Rafal R. Sicinski, Warsaw, Poland; Kato L. Perlman, Madison, Wis.

[73] Assignee: Wisconsin Alumni Research Foundation, Madison, Wis.

[21] Appl. No.: 811,165

[22] Filed: Mar. 4, 1997

Related U.S. Application Data

[60] Continuation of Ser. No. 441,795, May 16, 1995, abandoned, which is a division of Ser. No. 342,855, Nov. 21, 1994, abandoned.

[51] Int. Cl.$^6$ .................................................. A61K 31/59
[52] U.S. Cl. ............................................................. 514/167
[58] Field of Search ................................................ 514/167

[56] References Cited

U.S. PATENT DOCUMENTS

| 5,086,191 | 2/1992 | DeLuca et al. | 552/653 |
| 5,246,925 | 9/1993 | DeLuca et al. | 514/167 |
| 5,281,731 | 1/1994 | DeLuca et al. | 552/653 |
| 5,321,018 | 6/1994 | DeLuca | 514/167 |
| 5,342,975 | 8/1994 | DeLuca et al. | 552/653 |
| 5,449,668 | 9/1995 | Sestelo et al. | 514/167 |

FOREIGN PATENT DOCUMENTS

| 387077 | 9/1990 | European Pat. Off. | A61K 31/59 |
| 474517 | 3/1992 | European Pat. Off. | A61K 31/59 |
| 0516410 | 12/1992 | European Pat. Off. | |
| 0582481 | 2/1994 | European Pat. Off. | |
| 0664287 | 7/1995 | European Pat. Off. | |
| WO95/01960 | 1/1995 | WIPO | |

OTHER PUBLICATIONS

Biorganic & Medicinal Chemistry Letters, vol. 3, No. 9, pp. 1855–1858, 1993, "Synthesis and Biological Evaluation of 18–Substituted Analogs of 1α,25–Dihydroxyvitamin $D_3$", Nilsson et al.

J. Org. Chem., vol. 57, No. 11, pp. 3214–3217, 1992, "18–Substituted Derivatives of Vitamin D: 18–Acetoxy–1α, 25–Dihydroxyvitamin $D_3$ and Related Analogues", Maynard et al.

*Primary Examiner*—Kimberly J. Prior
*Attorney, Agent, or Firm*—Andrus, Sceales, Starke & Sawall

[57] ABSTRACT

18,19-dinor-vitamin $D_3$ analogs in which the angular methyl group attached to carbon 13 of the CD-ring and the exocyclic methylene group attached to carbon 10 of the A-ring have been removed and replaced by a hydrogen atom. The 18,19-dinor vitamin D compounds are characterized by relatively high cell differentiation activity, and marked intestinal calcium transport activity while exhibiting lower activity than 1α,25-dihydroxyvitamin $D_3$ in their ability to mobilize calcium from bone. These compounds would be useful for the treatment of diseases where bone formation is desired, such as osteoporosis, because of their preferential calcemic activity, and for the treatment of psoriasis due to their cell differentiation activity.

3 Claims, No Drawings

18,19-DINOR-VITAMIN D COMPOUNDS

This application is a continuation of application Ser. No. 08/441,795 filed May 16, 1995, now abandoned, which in turn is a division of application Ser. No. 08/342,855 filed Nov. 21, 1994, now abandoned.

This invention was made with United States Government support awarded by the National Institutes of Health (NIH), Grant No. DK-14881. The United States Government has certain rights in this invention.

BACKGROUND OF THE INVENTION

The natural hormone, $1\alpha,25$-dihydroxyvitamin $D_3$ and its analog in ergosterol series, i.e. $1\alpha,25$-dihydroxyvitamin $D_2$ are known to be highly potent regulators of calcium homeostasis in animals and humans, and more recently their activity in cellular differentiation has been established, V. Ostrem et al, *Proc. Natl. Acad. Sci. USA*, 84, 2610 (1987). Many structural analogs of these metabolites have been prepared and tested, including $1\alpha$-hydroxyvitamin $D_3$, $1\alpha$-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases as renal osteodystrophy, vitamin D-resistant rickets, osteoporosis, psoriasis, and certain malignancies.

Recently, a new class of vitamin D analogs has been discovered, i.e. so called 19-nor-vitamin D compounds, which are characterized by the replacement of the ring A exocyclic methylene group (carbon 19), typical of the vitamin D system, by hydrogen atoms. Biological testing of such 19-nor-analogs (e.g. $1\alpha,25$-dihydroxy-19-nor-vitamin $D_3$) revealed a selective activity profile with high potency in inducing cellular differentiation, with very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al. *Tetrahedron Letters* 31, 1823 (1990); Perlman et al. *Tetrahedron Letters* 32, 7663 (1991), and DeLuca et al. U.S. Pat. No. 5,086,191).

In a continuing effort to explore the 19-nor class of pharmacologically important vitamin D compounds, their analogs lacking the C-18 angular methyl group, i.e. 18,19-dinor-vitamin D compounds have now been synthesized and tested.

DISCLOSURE OF THE INVENTION

A class of $1\alpha$-hydroxylated vitamin D compounds not known heretofore are the 18,19-dinor-analogs, i.e. compounds in which the C-18 angular methyl substituent (carbon 18) normally attached to carbon 13 of the CD-ring and the C-19 exocyclic methylene group (carbon 19) normally attached to carbon 10 of the A-ring which are typical of all vitamin D systems have been removed and replaced by hydrogen atoms. Structurally these novel analogs are characterized by the general formula I shown below:

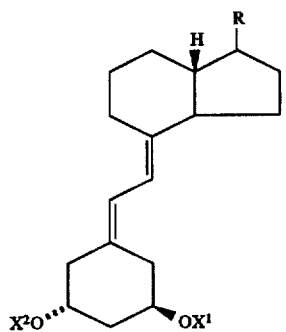

where $X^1$ and $X^2$, which may be the same or different, are each selected from hydrogen and a hydroxy protecting group, and where the group R represents any of the typical side chains known for vitamin D type compounds.

More specifically R can represent a saturated or unsaturated hydrocarbon radical of 1 to 35 carbons, that may be straight-chain, branched or cyclic and that may contain one or more additional substituents, such as hydroxy- or protected-hydroxy groups, fluoro, carbonyl, ester, epoxy, amino or other heteroatomic groups. Preferred side chains of this type are represented by the structure below.

where the stereochemical center (corresponding to C-20 in steroid numbering) may have the $\underline{R}$ or $\underline{S}$ configuration, (i.e. either the natural configuration about carbon 20 or the 20-epi configuration), and where Z is selected from Y, —OY, —$CH_2OY$, —C≡CY and —CH=CHY, where the double bond may have the cis or trans geometry, and where Y is selected from hydrogen, methyl, —$CR_5O$ and a radical of the structure:

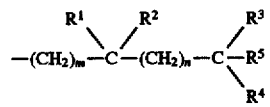

where m and n, independently, represent the integers from 0 to 5, where $R^1$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where $R^1$ and $R^2$, taken together, represent an oxo group, or an alkylidene group, =$CR^2R^3$, or the group —$(CH_2)_p$—, where p is an integer from 2 to 5, and where $R^3$ and $R^4$, taken together, represent an oxo group, or the group —$(CH_2)_q$—, where q is an integer from 2 to 5, and where $R^5$ represents hydrogen, hydroxy, protected hydroxy, or $C_{1-5}$ alkyl and wherein any of the CH-groups at positions 20, 22, or 23 in the side chain may be replaced by a nitrogen atom, or where any of the groups —$CH(CH_3)$—, —$CH(R^3)$—, or —$CH(R^2)$— at positions 20, 22, and 23, respectively, may be replaced by an oxygen or sulfur atom.

Specific important examples of side chains are the structures represented by formulas (a), (b), (c), (d) and (e) below. i.e. the side chain as it occurs in 25-hydroxyvitamin $D_3$ (a);

vitamin D$_3$ (b); 25-hydroxyvitamin D$_2$ (c); vitamin D$_2$ (d); and the C-24 epimer of 25-hydroxyvitamin D$_2$ (e).

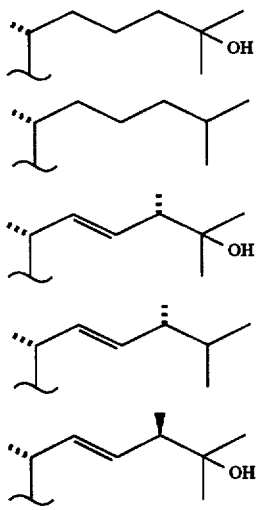

The above novel compounds exhibit a desired, and highly advantageous, pattern of biological activity. These compounds are characterized by a marked intestinal calcium transport activity, as compared to that of 1α, 25-dihydroxyvitamin D$_3$, while exhibiting lower activity than 1α,25-dihydroxyvitamin D$_3$ in their ability to mobilize calcium from bone. Hence, these compounds are highly specific in their calcemic activity. Their preferential activity on intestinal calcium transport and reduced calcium mobilizing activity in bone allows the in vivo administration of these compounds for the treatment of metabolic bone diseases where bone loss is a major concern. Because of their preferential calcemic activity, these compounds would be preferred therapeutic agents for the treatment of diseases where bone formation is desired, such as osteoporosis, osteomalacia and renal osteodystrophy. The treatment may be transdermal, oral or parenteral. The compounds may be present in a composition in an amount from about 0.1 µg/gm to about 50 µg/gm of the composition, and may be administered in dosages of from about 0.1µ/day to about 50 µg/day.

The above compounds are also characterized by high cell differentiation activity. Thus, these compounds also provide therapeutic agents for the treatment of psoriasis. The compounds may be present in a composition to treat psoriasis in an amount from about 0.01 µg/gm to about 100 µg/gm of the composition, and may be administered topically, orally or parenterally in dosages of from about 0.01 µg/day to about 100 µg/day.

This invention also provides novel intermediate compounds formed during the synthesis of the end products.

BRIEF DESCRIPTION OF THE DRAWINGS

FIG. 1 is a graph illustrating the percent HL-60 cell differentiation as a function of the concentration of 18,19-dinor-1α,25-dihydroxyvitamin D$_3$, 19-nor-1α,25-dihydroxyvitamin D$_3$ and 1α,25-dihydroxyvitamin D$_3$; and FIG. 2 is a graph illustrating the relative activity of 18-nor-1α,25-dihydroxyvitamin D$_3$, 19-nor-1α,25-dihydroxyvitamin D$_3$, 18,19-dinor-1α,25-dihydroxyvitamin D$_3$, and 1α,25-dihydroxyvitamin D$_3$ in binding to the 1,25-dihydroxyvitamin D pig intestinal nuclear receptor.

DETAILED DESCRIPTION OF THE INVENTION

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. Alkoxyalkyl protecting groups are groupings such a methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals.

A "protected hydroxy" group is a hydroxy group protected by any group commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively.

The preparation of 1α-hydroxy-18,19-dinor-vitamin D compounds having the basic structure I can be accomplished by a common general method, i.e. the condensation of the ring A synthon II with a bicyclic Windaus-Grundmann type ketone III:

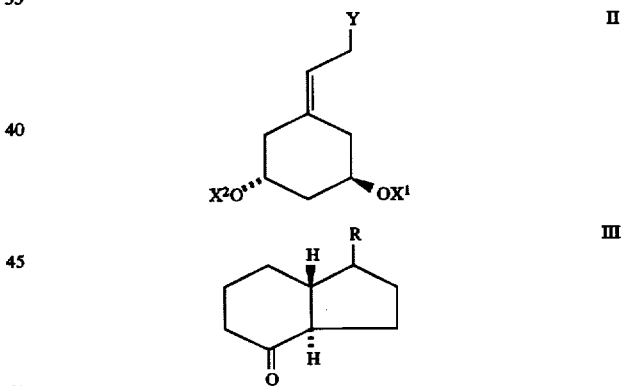

In the structures II and III, groups X$^1$, X$^2$ and R represent groups defined above; X$^1$ and X$^2$ are preferably hydroxy-protecting groups, it being also understood that any functionalities in R that might be sensitive, or that interfere with the condensation reaction, be suitable protected as is well-known in the art. Compounds of the general structure III, where Y is —POPh$_2$, PO(Alkyl)$_2$, or — SO$_2$Ar, or —Si (Alkyl)$_3$ can be prepared by described method (DeLuca et al., Eur. Pat. Appl. EP 0 516 410 A2). Phosphine oxide of structure II, with tert-butyldimethylsilyl groups as X$^1$ and X$^2$, is the known compound, [Perlman et al., Tetrahedron Letters 32, 7663 (1991)] which can be succesfully used for the above condensation. The process shown above represents an application of the convergent synthesis concept, which has been applied effectively for the preparation of vitamin D compounds [e.g. Lythgoe et al., J. Chem. Soc. Perkin Trans. I, 590 (1978); Lythgoe, Chem. Soc. Rev. 9, 449

(1983); Toh et al., *J. Org. Chem.* 48, 1414 (1983); Baggiolini et al., *J. Org. Chem.* 51, 3098 (1986); Sardina et al., *J. Org. Chem.* 51, 1264 (1986); *J. Org. Chem.* 51, 1269 (1986)].

For the preparation of the 18-nor CD ketones of general structure III, a new synthetic route has been developed, based on the Windaus-Grundmann type ketones of the general structure IV as starting materials. Required CD-ring ketones IV are known, or can be prepared by known methods. Specific important examples of such known bicyclic ketones are the structures with the side chains (a), (b), (c) and (d) described above, i.e. 25-hydroxy Grundmann's ketone (e) [Baggiolini et al., *J. Org. Chem*, 51, 3098 (1986)]; Grundmann's ketone (f) [Inhoffen et al., *Chem. Ber.* 90, 664 (1957)]; 25-hydroxy Windaus ketone (g) [Baggiolini et al., *J. Org. Chem.*, 51, 3098 (1986)] and Windaus ketone (h) [Windaus et al., *Ann.*, 524, 297 (1936)]:

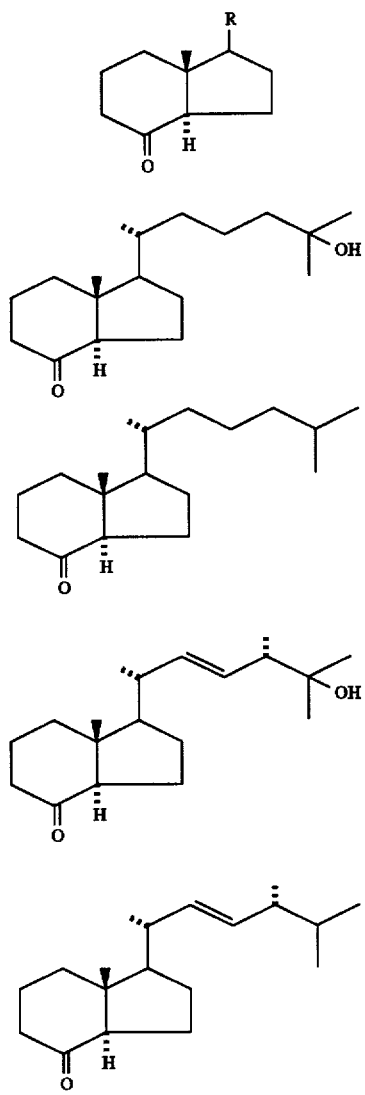

The overall process of transformation of the starting bicyclic ketones IV into their 18-nor analogs III, in general form, is summarized by the reaction scheme below:

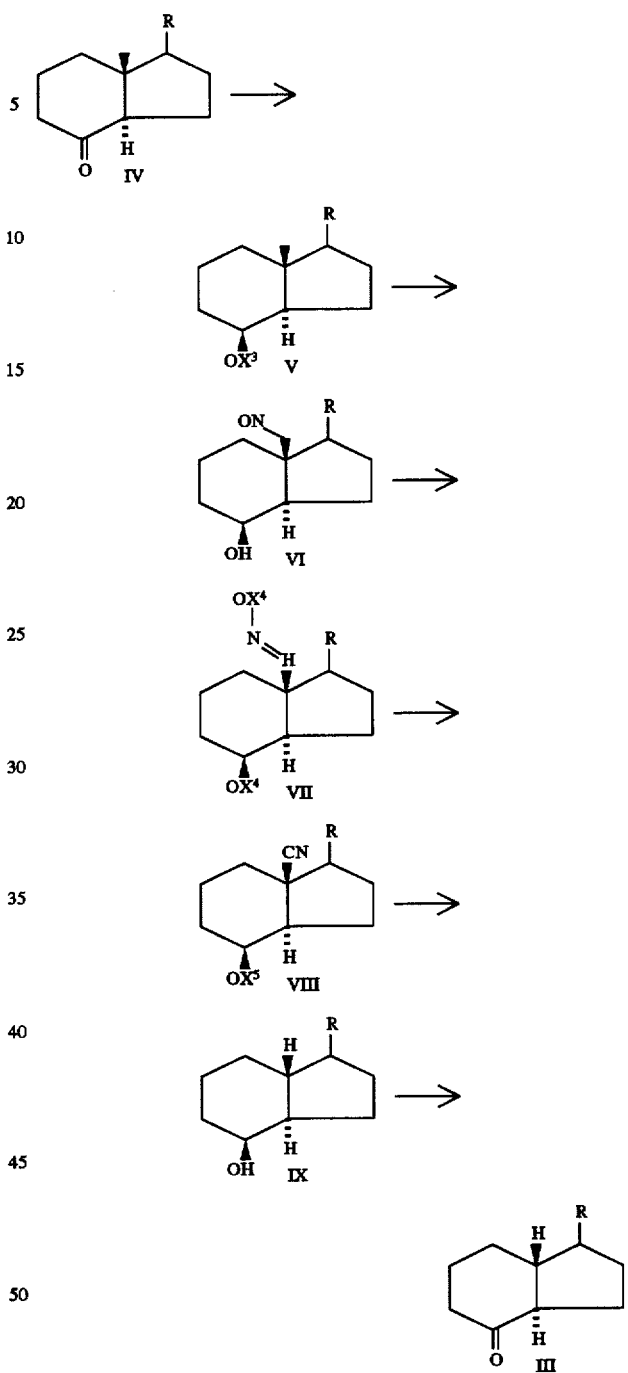

As shown in this scheme, first step of the synthesis comprises the reduction of the 8-keto group in IV to the axial 8β-hydroxy CD-fragment V ($X^3$=H). Such stereoselective reduction process is well known and can be easily accomplished using, for example, $LiAlH_4$ or $NaBH_4$. It is understood that hydroxy groups in the side chain R of ketone IV, if present, should be approppriately protected before the reduction process, and the protecting groups selected are both compatible with subsequent chemical transformations, and also removable, if desired. Suitable are, for example, alkylsilyl- and arylsilyl groups or alkoxyalkyl groups.

The axial orientation of the C-8 hydroxy group in V ($X^3$=H), being sterically fixed in the trans-hydrindane system, in close proximity to the angular methyl group at C-13, is crucial for the successful intramolecular free radical reaction leading to 18-functionalized compounds. It has been established that efficiency of the abstraction of a hydrogen atom from the angular methyl group in steroids strongly depends on the distance of the oxy radical from the hydrogen atoms of the angular methyl groups. The rate of hydrogen abstraction reaches a maximum at internuclear distances between oxygen and the methyl carbon of 2.5–2.7Å and decreases rapidly at distances over 3Å. Our molecular modeling studies show that in the case of 8β-alcohols V ($X^3$=H) the distance C(18)-O is smaller than 3Å (usually ca. 2.96Å) and, therefore, these compounds fulfill all requirements for successful functionalization at C-18. As a method of angular methyl group functionalization a photolysis of nitrites (Barton reaction) has been chosen. Thus, alcohols of general structure V ($X^3$=H) are converted into the corresponding nitrites V ($X^3$=NO) by one of the existing methods, including treatment with nitrosyl chloride in pyridine and trans-esterification with tert-butyl nitrite or isopentyl nitrite. The former method has a more general applicability but requires the use of expensive gaseous nitrosyl chloride. The latter, nitrosyl exchange method, can be recomended due to its simplicity. The next step of the synthesis consisted of the photolysis of V ($X^3$=NO) resulting in the intramolecular exchange of the NO of the nitrite residue with hydrogen atom attached to C-18. The C-nitroso compound VI thus formed rearranges to hydroxy oxime VII ($X^4$=H) either spontaneously or by heating in a solvent such as 2-propanol. Nitrite V ($X^3$=NO) photolysis can be in general performed under oxygen-free atmosphere in an irradiation apparatus with a water-cooled central sleeve into which the mercury lamp equipped with pyrex filter is introduced and efficient cooling is used to keep the temperature of the irradiated solution between 0° and 10° C. The drop in yield, due to competing intermolecular hydrogen abstraction reactions (regenerating the starting alcohol), can be suppressed by using solvents which do not contain easily abstractable hydrogen atoms, e.g. benzene. Although 18-nitroso compounds of general structure VI usually isomerize rapidly to the 18-oximes VII ($X^4$=H), it is recommended that rearrangement be completed by brief treatment of the crude irradiation product in boiling 2-propanol.

The subsequent steps of the process comprise the transformation of 8β-hydroxy oxime VII ($X^4$=H) into the 8β-hydroxy nitrile VIII ($X^5$=H). This conversion can be easily achieved by the thermal elimination of the elements of acetic acid from the acetyl derivative VII ($X^4$=Ac) folowed by hydrolysis of 8β-acetoxy group in the resulting acetoxy nitrile VIII ($X^5$=Ac). The transformation of hydroxy oxime VII ($X^4$=H) to VIII ($X^5$=Ac) can be done in two steps: acetylation of VII ($X^4$=H) under standard conditions (acetic anhydride in pyridine) to diacetate VII ($X^4$=Ac) and subsequent thermal reaction (pyrolysis) of the latter resulting in the elimination of acetic acid molecule from the acetoxy-imino group and formation of the nitrile VIII ($X^5$=Ac). Alternatively, the conversion of VII ($X^4$=H) to VIII ($X^5$=Ac) can be much easier accomplished by heating the oxime in acetic anhydride (addition of sodium or potassium acetate is sometimes helpful).

The hydrolysis of 8β-acetoxy group in the nitrile VIII ($X^5$=Ac) producing the corresponding alcohol VIII ($X^5$=H) can be performed under standard basic conditions. This process is desired in view of the following chemical transformation, i.e. reductive removal of the C-13 cyano group. Conditions required for such decyanation process could otherwise cause the reduction of the 8-acetoxy group to the corresponding alkane (8-unsubstituted derivative). 8β-Hydroxy group in VIII ($X^5$=H) can be protected as alkylsilyl-, arylsilyl or alkoxyalkyl ether during the decyanation process, if desired. It is understood, however, that such protecting group has to be selectively deprotectable (in the presence of other protected hydroxy groups in R, if any) at the next stage of the synthesis. Several methods for the reductive decyanation of VIII ($X^5$=H) are available, the most important being dissolving metal reductions. Thus, for example, VIII ($X^5$=H) can be transformed into 18-nor derivative IX by reaction with potassium metal in hexamethylphosphoric triamide and tert-butanol or using potassium metal/dicyclohexano-18-crown-6/toluene system.

The following synthetic step comprises the oxidation of 18-nor-8β-alcohol IX to the desired 8-keto compound III. Several oxidation methods can be used providing they do not cause epimerization at C-14 in the formed product. Methods recommended for their ability to preserve a chiral center next to 8-keto group include oxidation with $CrO_3$-pyridine, $SO_3$-$Me_2SO$ and PDC reagents. Keto compound III can be directly used in the next Wittig-Horner reaction giving 18,19-dinor-vitamin D derivatives I or, before the coupling step, it can be transformed to another compound with different side chain R. In the case where R is a saturated side chain, for example cholestane side chain (b) (18-nor Grundmann's ketone), there is a possibility to perform selective hydroxylation of the unhindered tertiary carbon atom (C-25 in the case of cholestane side chain) using ruthenium tetroxide [Kiegiel et al., *Tetrahedron Letters* 32, 6057 (1991)] or dioxirane [Bovicelli et al., *J. Org. Chem.*, 57, 5052 (1992)] oxidation methods. If desired, 8β-alcohol IX can be subjected to side chain hydroxylation process because, under the reaction conditions, rapid oxidation of a secondary hydroxy group at C-8 takes place.

The condensation reaction is advantageously conducted by treating the A ring-unit of general structure II, dissolved in an organic solvent, with a strong base (e.g. an alkali metal hydride, alkyl- or aryl lithium, or a lithium alkylamide reagent), so as to generate the anion of II, and then allowing this anion to react with 18-nor-ketone III, so as to achieve condensation to the 18,19-dinor-vitamin D analog I, either directly, or via intermediates (e.g. in the case of condensation with compound II where Y=$SO_2$Ar) transformable to I according to known procedures. Any hydroxy-protecting groups (i.e. protecting groups $X^1$ and $X^2$ and/or hydroxy-protecting groups that may be present in the side chain R) can then be removed by appropriate hydrolytic or reductive procedures known in the art to obtain the free hydroxyvitamin analog, structure I, where $X^1$ and $X^2$ represent hydrogen.

Synthesis of 1α,25-dihydroxy-18,19-dinor-vitamin $D_3$

EXAMPLE 1

Preparation of des-A,B-cholestan-8β-yl nitrite (4) (Scheme 1)

A solution of Grundmann's ketone 2 [(2.70 g, 10.2 mmol; obtained by ozonolysis of commercial vitamin $D_3$ (1)] in anhydrous ether (90 mL) at 0° C. was added to a slurry of $LiAlH_4$ (3.89 g, 102.5 mmol) in anhydrous ether (270 mL). The reaction mixture was stirred at 0° C. for 1 h, and ethyl acetate (27 mL) followed by cold 10% $H_2SO_4$ (100 mL) was used to destroy the unreacted $LiAlH_4$ and complete the hydrolysis. The resulting mixture was extracted with ether, the combined extracts were washed with water and brine, dried (Na$_2$SO$_4$) and evaporated. The product was purified by flash chromatography on silica. Elution with 10% ethyl acetate in hexane gave the known 8β-alcohol 3 as a colorless oil (2.42 g, 89%): $^1$H NMR (CDCl$_3$, 500 MHz) δ0.865 (6H, br d, J~6 Hz, 26- and 27-H$_3$), 0.891 (3H, d, J=6.4 Hz, 21-H$_3$), 0.929 (3H, s, 18-H$_3$), 4.07 (1H, m, w/2=10 Hz, 8α-H); MS m/z (relative intensity) 266 (M$^+$, 9), 251 (3), 207 (12), 164 (19), 111 (61), 91 (100).

A solution of alcohol 3 (533 mg, 2 mmol) in chloroform (10 mL) was treated with tert-butyl nitrite (2.2 mL) and stirred at room temperature in the dark for 40 min. Benzene (20 mL) was added and the solvents were rapidly evaporated under vacuum (temperature of water bath 40° C.). During evaporation of solvents and further high-vacuum drying the nitrite was protected from light. The oily product contained traces of starting alcohol 3 but it was suitable for the subsequent reaction. The nitrite 4 possessed the following spectral characteristics: IR (CHCl$_3$) 1632 (nitrite) cm$^{-1}$; $^1$H NMR (CDCl$_3$, 500 MHz) δ 0.767 (3H, s, 18-H$_3$), 0.862 (6H, br d, J=6.2 Hz, 26- and 27-H$_3$), 0.901 (3H, d, J=7.0 Hz, 21-H$_3$), 5.76 (1H, narr m, 8α-H).

EXAMPLE 2

Synthesis of 18-(hydroxyimino)-des-A,B-cholestan-8β-ol (6)

The crude nitrite ester 4 obtained from 2 mmol of 8β-alcohol 3 (see Example 1) was dissolved in anhydrous benzene (140 mL) and irradiated, in the apparatus consisting of a Pyrex vessel and a water-cooled Vycor immersion well, with Hanovia high pressure mercury arc lamp equipped with a Pyrex filter. Slow stream of argon was passed into the vessel and the temperature of the solution was maintained at 10° C. After 1 h 40 min of the irradiation TLC showed only traces of unreacted nitrite. The reaction mixture was allowed to stand overnight at room temperature (in order to accomplish an isomerization of the intermediate 19-nitroso compound 5 to the oxime), benzene was evaporated under vacuum and the oily residue was subjected to flash chromatography. Elution with 30% ethyl acetate in hexane afforded pure oxime 6 (270 mg, 46% from 8β-alcohol 3) as a colorless oil: IR (CHCl$_3$) 3590, 3240, 3140 (OH) cm$^{-1}$; $^1$H NMR (CDCl$_3$) δ 0.865 (6H, d, J=6.1 Hz, 26- and 27-H$_3$), 0.994 (3H, d, J=6.7 Hz, 21-H$_3$), 4.04 (1H, m, w/2=9 Hz, 8α-H), 6.29 (1H, br s, OH) 7.36 (1H, s, 18-H), 10.38 (1H, br s, OH); MS m/z (relative intensity) 295 (M$^+$, 16), 278 (87), 260 (68), 245 (33), 183 (100); exact mass calcd for C$_{18}$H$_{33}$O$_2$N 295.2511, found 295.2514.

EXAMPLE 3

Conversion of oxime 6 into 8β-acetoxy-des-A,B-cholestane-18-nitrile (8)

(a) A solution of the oxime 6 (120 mg, 0.41 mmol) in acetic anhydride (5 mL) was refluxed for 1.5 h. The reaction mixture was cooled, poured carefully on ice and extracted with benzene. Extracts were combined, washed with water, NaHCO$_3$ and brine, dried (Na$_2$SO$_4$) and evaporated. The oily residue was purified by flash chromatography using 10% ethyl acetate in hexane. Pure acetoxy nitrile 8 (112 mg, 86%) was obtained as a colorless oil: IR (CHCl$_3$) 2220 (nitrile), 1720 and 1240 acetate) cm$^{-1}$; $^1$H NMR (CDCl$_3$) δ 0.864 (6H, d, J=6.2 Hz, 26- and 27-H$_3$), 1.032 (3H, d, J=6.5 Hz, 21-H$_3$), 2.13 (3H, s, OAc), 5.20 (1H, m, w/2=8 Hz, 8α-H); MS m/z (relative intensity) 319 (M$^+$, 56), 304 (18), 277 (89), 259 (100), 244 (64); exact mass calcd for C$_{20}$H$_{33}$O$_2$N 319.2511, found 319.2506.

(b) Hydroxy oxime 6 (120 mg, 0.41 mmol) was heated with acetic anhydride (0.3 mL) and pyridine (0.5 mL) for 36 h at 60° C. The reaction mixture was cooled, poured on ice and extracted with benzene. Extracts were combined, washed with water, NaHCO$_3$ and brine, dried (Na$_2$SO$_4$) and evaporated. The oily residue was purified by flash chromatography using 10% ethyl acetate in hexane. Pure acetoxy nitrile 8 (109 mg, 84%) was obtained as a colorless oil.

Monitoring of the reaction mixture with TLC showed a presence of a spot corresponding to diacetate 7.

EXAMPLE 4

Hydrolysis of the acetoxy nitrile 8 to 8β-hydroxy-des-A,B-cholestane-18-nitrile (9)

Acetoxy nitrile 8 (210 mg, 0.66 mmol) was treated with 10% methanolic KOH (10 mL) at 50° C. for 1.5 h. After concentration under vacuum the reaction mixture was poured into water and extracted with benzene and ether. The organic extracts were combined, washed with brine, dried (Na$_2$SO$_4$) and evaporated. The residue was redissolved in hexane/ethyl acetate (7:3) and the solution passed through a silica gel Sep-Pak cartridge. Evaporation of solvents gave pure hydroxy nitrile 9 (175 mg, 96%) as an oil: IR (CHCl$_3$) 3600 (OH), 2220 (nitrile) cm$^{-1}$; $^1$H NMR (CDCl$_3$) δ 0.868 (6H, d, J=6.0 Hz, 26- and 27-H$_3$), 1.032 (3H, d, J=7.1 Hz, 21-H$_3$), 4.10 (1H, m, w/2=10 Hz, 8α-H); MS m/z (relative intensity) 277 (M$^+$, 37), 262 (28), 244 (18), 234 (26), 220 (32), 206 (87), 121 (100); exact mass calcd for C$_{18}$H$_{31}$ON 277.2406, found 277.2406.

EXAMPLE 5

Reductive decyanation of hydroxy nitrile 9 to des-A,B-18-norcholestan-8β-ol (10)

(a) To a stirred mixture of potassium (55 mg, 1.4 mmol) in hexamethylphosphoric triamide (HMPA, 170 μL) and ether (420 μL) a solution of the hydroxy nitrile 9 (55 mg, 0.2 mmol) in tert-butanol (50 μL) and ether (200 μL) was added dropwise at 0° C. under argon. Cooling bath was removed and the brown-yellow solution was stirred at room temperature for 5 h under argon. Unreacted potassium was removed, the mixture was diluted with benzene, few drops of 2-propanol were added and water. The organic phase was washed with water, dried (Na$_2$SO$_4$) and evaporated. The residue was purified by flash chromatography. Elution with 10% ethyl acetate in hexane gave pure alcohol 10 (38 mg, 76%) as a colorless oil: IR (CHCl$_3$) 3630 and 3470 (OH) cm$^{-1}$; $^1$H NMR (CDCl$_3$) δ 0.863 and 0.868 (3H and 3H, each d, J=6.3 Hz, 26- and 27-H$_3$), 0.881 (3H, d, J=6.5 Hz, 21-H$_3$), 4.05 (1H, m, w/2=8 Hz, 8α-H); 1H NMR (C$_6$D$_6$) δ 0.901 and 0.907 (3H and 3H, each d, J=6.2 Hz, 26- and 27-H$_3$), 0.945 (3H, d, J=6.5 Hz, 21-H$_3$), 3.80 (1H, m, w/2=8 Hz, 8α-H) ; $^{13}$C NMR (CDCl$_3$) δ 18.1 (q), 20.3 (t), 22.5 (q), 22.7 (q), 24.8 (t), 25.4 (t), 25.6 (t), 27.9 (d), 31.7 (t), 33.5 (t+t), 35.1 (d), 39.3 (t), 39.6 (d), 49.8 (d), 50.7 (d), 67.9 (d); MS m/z (relative intensity) 252 (M$^+$, 1), 234 (3), 219 (2), 121 (100); exact mass calcd for C$_{17}$H$_{32}$O 252.2453, found 252.2470.

(b) A lump (ca. ¼ cm$^3$) of potassium metal was added to a solution of hydroxy nitrile 9 (55 mg, 0.2 mmol) and dicyclohexano-18-crown-6 (111 mg, 0.3 mmol) in anhydrous toluene (8 mL). The mixture was stirred under argon at room temperature for 10 h, unreacted potassium was removed, few drops of 2-propanol were added and water. The organic phase was washed with water, dried ($Na_2SO_4$) and evaporated. The residue was subjected to flash chromatography. Elution with 10% ethyl acetate in hexane gave alcohol 10 (30 mg) which was subsequently purified by HPLC (10 mm×25 cm Zorbax-Sil column, 4 mL/min) using hexane/ethyl acetate (9:1) solvent system. Pure compound 10 (25 mg, 50%) was eluted at $R_V$ 44 mL as a colorless oil.

EXAMPLE 6

Oxidation of alcohol 10 to des-A,B-18-norcholestan-8-one (11) and 25-hydroxy-des-A,B-18-norcholestan-8-one (12)

(a) To a solution of alcohol 10 (5 mg, 20 µmol) in $CH_2Cl_2$ (2 mL) containing a catalytic amount of pyridinium p-toluenesulfonate (PPTS) was added pyridinium dichromate (PDC, 25 mg, 66 µmol) at 0° C. with stirring. After 10 min the cooling bath was removed and the mixture was stirred at room temperature for 5 h. The brown mixture was diluted with ether and filtered through a silica Sep-Pak that was washed with hexane/ethyl acetate (1:1). Evaporation of the solvents gave a crude ketone 11 which was further purified by HPLC (10mm×25 cm Zorbax-Sil column, 4 mL/min) using hexane/ethyl acetate (9:1) solvent system. Analytically pure compound 11 (4 mg, 80%) was eluted at $R_V$ 29 mL (Grundmann's ketone 2 was eluted at $R_V$ 31 mL in the same system): $[\alpha]^{22}_D$ +16.2° (c 0.31, $CHCl_3$); CD $\Delta\epsilon$ ($\lambda_{max}$): −0.76 (311), −1.32 (301), −1.34 (294), −0.92 (282), −1.33 (190); $^1H$ NMR ($CDCl_3$) δ 0.866 (6H, d, J=6.9 Hz, 26- and 27-$H_3$), 0.889 (3H, d, J=6.9 Hz, 21-$H_3$); $^{13}C$ NMR ($CDCl_3$) δ 18.0 (q), 21.5 (t), 22.5 (q), 22.7 (q), 25.4 (t+t), 27.8 (t), 27.9 (d), 30.6 (t), 33.2 (t), 34.8 (d), 39.3 (t), 41.5 (t), 50.8 (d), 50.9 (d), 58.3 (d), 212.0 (s); MS m/z (relative intensity) 250 ($M^+$, 80), 207 (44), 137 (100); exact mass calcd for $C_{17}H_{30}O$ 250.2297, found 250.2289.

(b) To the stirred solution of ruthenium (III) chloride hydrate (11.5 mg, 0.06 mmol) and $NaIO_4$ (263 mg, 1.23 mmol) in water (1.0 mL), a solution of alcohol 10 (85 mg, 0.34 mmol) in $CCl_4$-$CH_3CN$ (1:1, 1.5 mL) was added. The mixture was vigorously stirred for 72 h at room temperature. Few drops of 2-propanol were added, the mixture was poured into water and extracted with $CCl_4$/$CHCl_3$ solvent system. The combined organic extracts were washed with water, dried ($Na_2SO_4$) and evaporated to give an oily residue which was subjected to flash chromatography. Elution with 20% ethyl acetate in hexane gave 8-ketone 11 (16 mg, 19%). Subsequent elution with 40% ethyl acetate in hexane afforded impure 25-hydroxy ketone 12 (20 mg) which was subjected to HPLC (10 mm×25 cm Zorbax-Sil column, 4 mL/min) using hexane/ethyl acetate (6:4) solvent system. Analytically pure compound 12 (12.7 mg, 14%;) was eluted at $R_V$ 51 mL (25-hydroxy Grundmann's ketone was eluted at $R_V$ 50 mL in the same system) as an oil crystallizing on standing in the refrigerator: $^1H$ NMR ($CDCl_3$) δ 0.908 (3H, d, J=6.5 Hz, 21-$H_3$), 1.216 (6H, s, 26- and 27-$H_3$); $^{13}C$ NMR ($CDCl_3$) δ 18.0 (q), 21.5 (t), 22.3 (t), 25.4 (t), 27.8 (t), 29.3 (q+q), 30.6 (t), 33.5 (t), 34.8 (d), 41.5 (t), 44.2 (t), 50.8 (d), 50.9 (d), 58.3 (d), 71.0 (s), 211.9 (s); MS m/z (relative intensity) 266 ($M^+$, <1), 251 (6), 248 (60), 233 (16), 137 (100); exact mass calcd for $C_{17}H_{30}O_2$ 266.2246, found 266.2257.

EXAMPLE 7

Silylation of hydroxy ketone 12 to 25-[(triethylsilyl)oxy]-des-A,B-18-norcholestan-8-one (13)

A solution of the ketone 12 (5 mg, 19 µmol) and imidazole (15 mg, 220 µmol) in anhydrous DMF (150 µL) was treated with triethylsilylchloride (15 µL, 90 µmol). The mixture was stirred at room temperature under argon for 4 h. Ethyl acetate was added and water, and the organic layer separated. The ethyl acetate layer was washed with water and brine, dried ($MgSO_4$), filtered and evaporated. The residue was passed through a silica Sep-Pak in 10% ethyl acetate in hexane, and after evaporation purified by HPLC (9.4 mm×25 cm Zorbax-Sil column, 4 mL/min) using hexane/ethyl acetate (9:1) solvent system. Pure protected ketone 13 (3.6 mg, 50%) was eluted at $R_V$ 25 mL as a colorless oil: $^1H$ NMR ($CDCl_3$) δ 0.559 (6H, q, J=7.9 Hz, 3×$SiCH_2$), 0.896 (3H, d, J=7.6 Hz, 21-$H_3$), 0.939 (9H, t, J=7.9 Hz, 3×$SiCH_2C$$H_3$), 1.183 (6H, s, 26- and 27-$H_3$).

EXAMPLE 8

Preparation of 1α,25-dihydroxy-18,19-dinor-vitamin $D_3$ (16) (Scheme II)

[2-[(3R,5R)-3,5-Bis[(tert-butyldimethylsilyl)oxy]-cyclohexylidene]ethyl]diphenylphosphine oxide (14) (12 mg, 21 µmol) was dissolved in anhydrous THF (200 µL), cooled to −78° C. and n-BuLi (1.4M in hexanes, 15 µL, 21 µmol) added under argon with stirring. The solution turned deep orange. After stirring for 5 min at −78° C. the protected ketone 13 (3.0 mg, 7.9 µmol) was added in anhydrous THF (200 µL+100 µL). The mixture was stirred under argon at −78° C. for 1 h and at 0° C. for 16 h. Ethyl acetate was added and the organic phase washed with saturated $NH_4Cl$, 10% $NaHCO_3$ and brine, dried ($MgSO_4$) and evaporated. The residue was passed through a silica Sep-Pak in 10% ethyl acetate in hexane, and after evaporation purified by HPLC (9.4 mm×25 cm Zorbax-Sil column, 4 mL/min) using hexane-ethyl acetate (9:1) solvent system. Pure protected vitamin 15 (1.7 mg, 29%) was eluted as a colorless oil: $^1H$ NMR ($CDCl_3$) δ 0.045 and 0.054 (6H and 6H, each s, 4×$SiCH_3$), 0.557 (6H, q, J=7.9 Hz, 3×$SiCH_2$), 0.86–0.87 (21H, 21-$H_3$ and 2×Si-t-Bu), 0.939 (9H, t, J=7.9 Hz, 3×$SiCH_2$$CH_3$), 1.178 (6H, br s, 26- and 27-$H_3$), 2.84 (1H, br d, J=13.5 Hz, 9β-H), 4.07 (2H, br m, 1β- and 3α-H), 5.90 and 6.14 (1H and 1H, each d, J=11.1 Hz, 7- and 6-H).

Protected vitamin 15 described above (850 µg, 1.2 µmol) was dissolved in benzene (40 µL) and cation exchange resin (AG 50W-X4, 17 mg; prewashed with methanol) in methanol (200 µL) was added. The mixture was stirred at room temperature under argon for 18 h, filtered through a silica Sep-Pak and washed with 2-propanol. The solvent was evaporated and a crude vitamin 16 was purified by HPLC (10 mm×25 cm Zorbax-Sil column, 4 mL/min) using hexane/2-propanol (7:3) solvent system. Analytically pure compound 16 (366 µg, 81%) was eluted at $R_V$ 37 mL (1α,25-dihydroxy-19-nor-vitamin $D_3$ was eluted at $R_V$ 36 mL in the same system) as a white solid: UV (in EtOH) $\lambda_{max}$ 243, 251.5, 261 nm; $^1H$ NMR ($CDCl_3$) δ 0.879 (3H, d, J=6.5 Hz, 21-$H_3$), 1.208 (6H, s, 26- and 27-$H_3$), 4.07 and 4.11 (1H and 1H, each m, 1β- and 3α-H), 5.94 and 6.30 (1H and 1H, each d, J=11.2 Hz, 7- and 6-H); MS m/z (relative intensity) v; exact mass calcd for $C_{25}H_{42}O_3$ 390.3134, found 390.3139 v 390(M+,39), 372(62), 354(23), 259(42), 231(84), 175(25), 149(25), 133(53), 121(64), 69(100).

SCHEME I
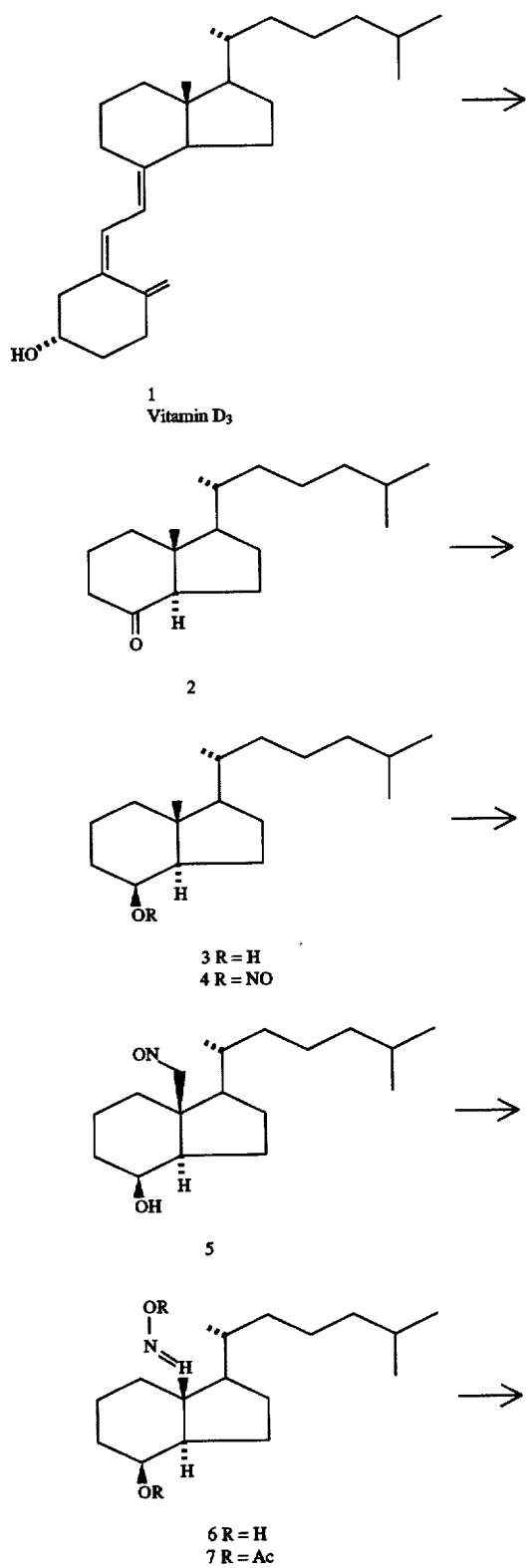
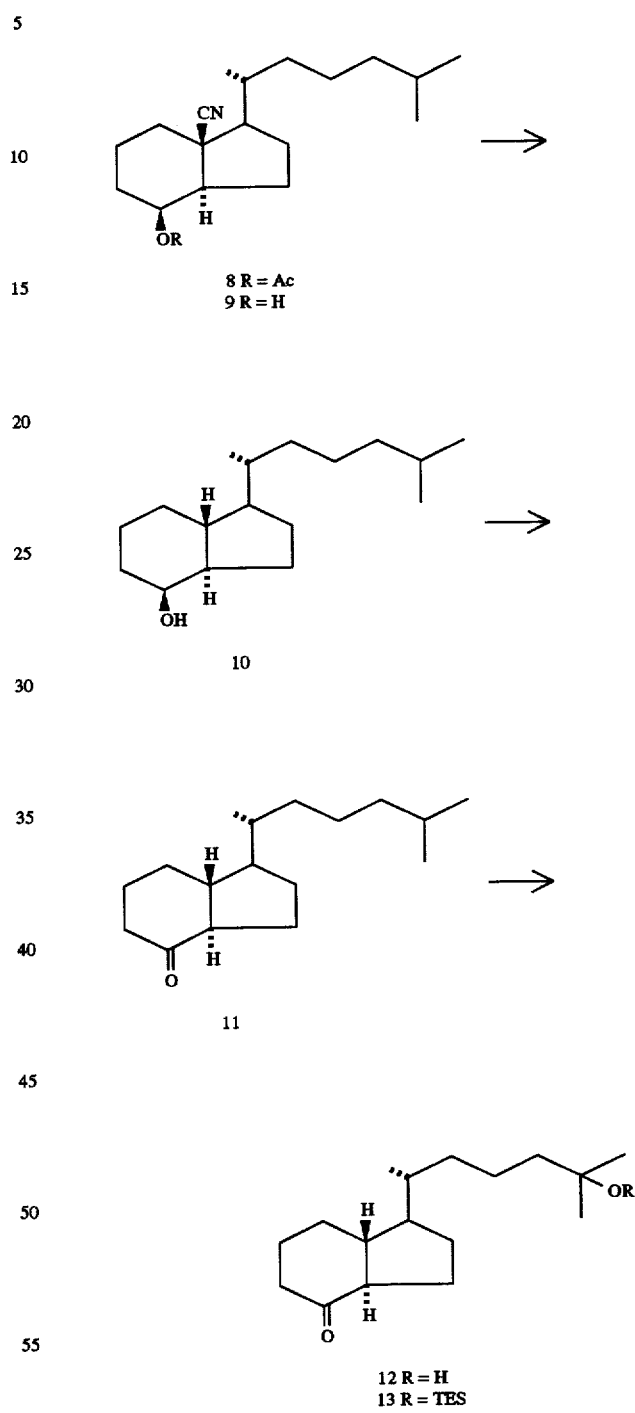

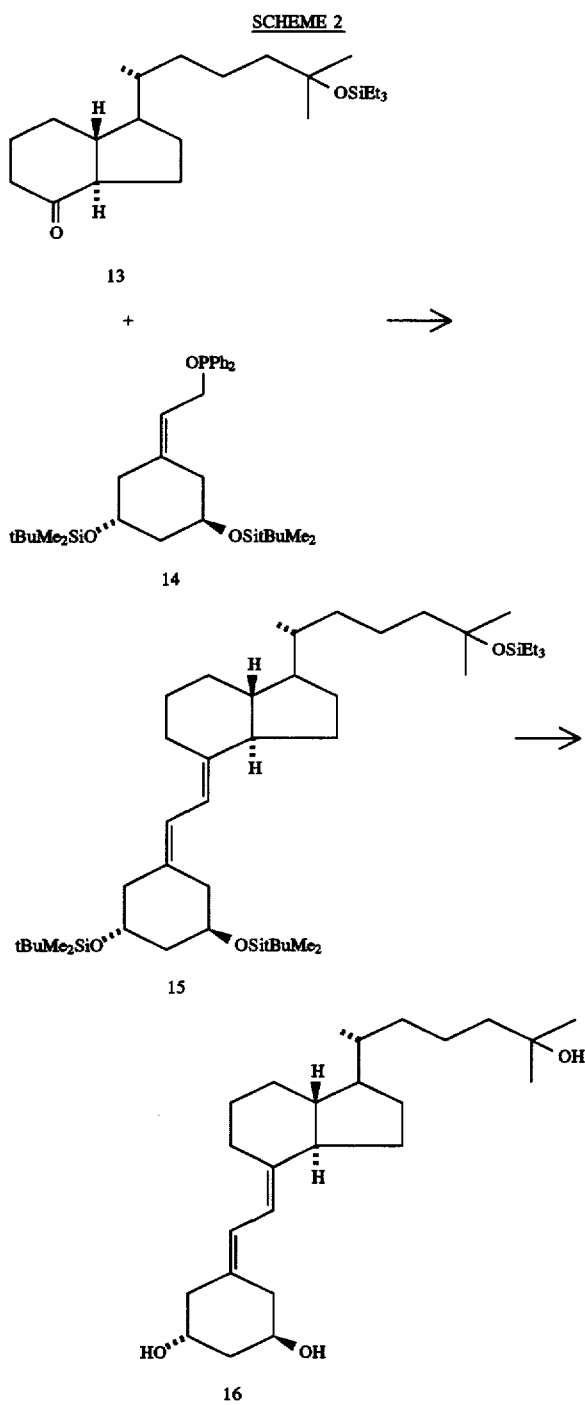

For treatment of bone diseases, the novel compounds of this invention defined by formula I may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds may be administered orally, parenterally or transdermally. The compounds are advantageously administered by injection or by intravenous infusion of suitable sterile solutions, or in the form of liquid or solid doses via the alimentary canal, or in the form of creams, ointments, patches, or similar vehicles suitable for transdermal applications. Doses of from 0.1 μg to 50 μg per day of the compounds are appropriate for treatment purposes, such doses being adjusted according to the disease to be treated, its severity and the response of the subject as is well understood in the art. Since the new compounds exhibit specificity of action, each may be suitably administered alone, or together with graded doses of another active vitamin D compound—e.g. 1α-hydroxyvitamin $D_2$ or $D_3$, or 1α,25-dihydroxyvitamin $D_3$—in suitations where different degrees of bone mineral mobilization and calcium transport stimulation is found to be advantageous.

Compositions for use in the above-mentioned treatment of psoriasis and other malignancies comprise an effective amount of one or more 18,19-dinor-vitamin D compound as defined by the above formula I as the active ingredient, and a suitable carrier. An effective amount of such compounds for use in accordance with this invention is from about 0.01 μg to about 100 μg per gm of composition, and may be administered topically, orally or parenterally in dosages of from about 0.01 μg/day to about 100 μg/day.

The compounds may be formulated as creams, lotions, ointments, topical patches, pills, capsules or tablets, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds may be administered topically, as oral doses, or parenterally by injection or infusion of suitable sterile solutions. The compounds are advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

Biological Activity of 18,19-Dinor-Vitamin D Compounds

The 18,19-dinor compounds of this invention exhibit a pattern of biological activity having high potency in promoting the differentiation of malignant cells, relatively high intestinal calcium transport activity and a relatively low ability to mobilize calcium from bone. This is illustrated by the biological assay results obtained for 1α,25-dihydroxy-18,19-dinor-vitamin $D_3$ which are summarized in FIGS. 1 and 2 and in Table 1 respectively. FIG. 1 shows a comparison of the activity of the known active metabolite 1α,25-dihydroxyvitamin $D_3$ and the 19-nor analog 1α,25-dihydroxy-19-nor-vitamin $D_3$ and the presently claimed 18,19-dinor-1α,25-dihydroxyvitamin $D_3$ in inducing the differentiation of human leukemia cells (HL-60 cells) in culture to monocytes. Differentiation activity was assesed by a standard differentiation assay, abbreviated in FIG. 1 as NBT reduction (nitroblue tetrazolium reduction). The assay was conducted according to known procedures, as given, for example, by DeLuca et al U.S. Pat. No. 4,717,721 and Ostrem et al, J. Biol. Chem. 262, 14164, 1987. For the assay, the differentiation activity of the test compounds is expressed in terms of the percent of HL-60 cells having differentiated to normal cells in response to a given concentration of test compound.

The results summarized in FIG. 1 clearly show that the analog, 1α,25-dihydroxy-18,19-dinor-vitamin $D_3$ is as potent as 1α,25-dihydroxyvitamin $D_3$ in promoting the differentiation of leukemia cells. Thus in the NBT assay close to 90% of the cells are induced to differentiate by 1α,25-dihydroxy-vitamin $D_3$ at a concentration of $1\times10^{-7}$ M, and the same degree of differentiation is achieved by the 18,19-dinor analog at $1\times10^{-7}$M.

FIG. 2 illustrates the relative activity of 18-nor-1α,25-dihydroxyvitamin $D_3$, 19-nor-1α,25-dihydroxyvitamin $D_3$, 18,19-dinor-1α,25-dihydroxyvitamin $D_3$ and 1α,25-dihydroxyvitamin $D_3$ in binding to the 1α,25-dihydroxyvitamin D pig intestinal nuclear receptor. FIG. 2 shows that 18,19-dinor-1α,25-dihydroxyvitamin $D_3$ is very active in binding to the 1α,25-dihydroxyvitamin $D_3$ receptor from porcine intestinal nuclei.

Table 1 shows a comparison of the calcemic activity of the known active metabolite 1α,25-dihydroxyvitamin $D_3$, and the 19-nor analog 1α,25-dihydroxy-19-nor-vitamin $D_3$ and the presently claimed 18,19-dinor-1α,25-dihydroxyvitamin $D_3$.

TABLE 1

INTESTINAL CALCIUM TRANSPORT AND BONE CALCIUM MOBILIZING ACTIVITIES OF 1α,25-DIHYDROXY-VITAMIN $D_3$ COMPOUNDS

| Compound | Dosage (Pmoles) | S/M (Ave. ± SEM) | Serum Ca (Ave. ± SEM) (mg/100 ml) |
|---|---|---|---|
| D deficient | 0 | 5.02 ± 0.22 | 4.83 ± 0.1 |
| 1,25(OH)$_2$D$_3$ | 1,000 | 13.5 ± 0.89 | 7.15 ± 0.24 |
| 19-Nor-1,25-(OH)$_2$D$_3$ | 1,000 | 10.4 ± 0.40 | 5.10 ± 0.14 |
| 18,19-Dinor-1,25-(OH)$_2$D$_3$ | 1,000 | 10.4 ± 0.85 | 5.66 ± 0.07 |

Male, weanling rats (Sprague-Dawley) were fed a low calcium vitamin D-deficient diet for three weeks and then received the indicated dose dissolved in 95% propylene glycol/5% ethanol intraperitoneally. 24 hours later, blood serum was obtained, and calcium determined in the presence of 0.1% lanthanum chloride, using an atomic absorption spectrometer. The control animals received the vehicle alone. The values are the mean ± standard error of the mean. There were at least 6 animals per group.

Table 1 shows that 18,19-dinor-1α,25-dihydroxyvitamin $D_3$, while having some ability to mobilize calcium from bone, is clearly not as active in this regard as 1α,25-dihydroxyvitamin $D_3$. Also, Table 1 shows that 18,19-dinor-1α,25-dihydroxyvitamin $D_3$ is almost as active as 1α,25-dihydroxyvitamin $D_3$ in intestinal calcium transport activity.

Thus, the 18,19-dinor analog shows a selective activity profile combining high potency in inducing the differentiation of malignant cells, relatively high intestinal calcium transport activity with relatively low bone mobilization activity. The compounds of this novel structural class, therefore, can be useful as therapeutic agents for the treatment of psoriasis and other malignancies, and for the treatment of metabolic bone diseases where bone loss is a major concern such as osteoporosis, osteomalacia and renal osteodystrophy.

Various modes of carry out the invention are contemplated as being within the scope of the following claims, particularly pointing out and distinctly claiming the subject matter regarded as the invention.

We claim:

1. A method of treating psoriasis comprising administering to a patient with said disease an effective amount of a compound having the formula:

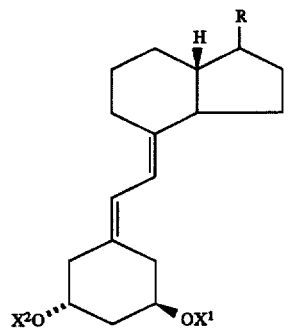

where $X^1$ and $X^2$, which may be the same or different, are each selected from hydrogen and a hydroxy protecting group, and where the group R is represented by the structure:

where the stereochemical center at carbon 20 may have the R or S configuration, and where Z is selected from Y, —OY, —CH$_2$OY, —C≡CY and —CH=CHY, where the double bond may have the cis or trans geometry, and where Y is selected from hydrogen, methyl, —CR$^5$O and a radical of the structure:

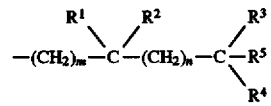

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group, =CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl, and wherein any of the groups at positions 20, 22, and 23, respectively, may be replaced by an oxygen atom.

2. The method of claim 1 wherein the compound is 18,19-dinor-1α,25-dihydroxyvitamin $D_3$.

3. The method of claim 1 wherein said effective amount comprises about 0.01 ug/day to about 100 ug/day of said compound.

* * * * *